(12) United States Patent
Grass et al.

(10) Patent No.: US 9,848,843 B2
(45) Date of Patent: Dec. 26, 2017

(54) DYNAMIC PERFUSION IMAGING

(75) Inventors: Michael Grass, Buchholz in der Nordheide (DE); Holger Schmitt, Hamburg (DE)

(73) Assignee: KONINKLIJKE PHILIPS N.V., Eindhoven (NL)

(*) Notice: Subject to any disclaimer, the term of this patent is extended or adjusted under 35 U.S.C. 154(b) by 905 days.

(21) Appl. No.: 14/112,047

(22) PCT Filed: Apr. 17, 2012

(86) PCT No.: PCT/IB2012/051914
§ 371 (c)(1),
(2), (4) Date: Oct. 16, 2013

(87) PCT Pub. No.: WO2012/143852
PCT Pub. Date: Oct. 26, 2012

(65) Prior Publication Data
US 2014/0037046 A1 Feb. 6, 2014

Related U.S. Application Data

(60) Provisional application No. 61/476,462, filed on Apr. 18, 2011.

(51) Int. Cl.
*A61B 6/00* (2006.01)

(52) U.S. Cl.
CPC .............. *A61B 6/481* (2013.01); *A61B 6/00* (2013.01); *A61B 6/486* (2013.01); *A61B 6/507* (2013.01); *A61B 6/5217* (2013.01); *A61B 6/542* (2013.01); *A61B 6/545* (2013.01); *A61B 6/503* (2013.01); *F04C 2270/0421* (2013.01)

(58) Field of Classification Search
CPC ......... A61B 6/032; A61B 6/469; A61B 6/481; A61B 6/542
See application file for complete search history.

(56) References Cited

U.S. PATENT DOCUMENTS

| | | | |
|---|---|---|---|
| 6,201,986 | B1 | 3/2001 | Riederer et al. |
| 6,556,856 | B1 | 4/2003 | Mistretta et al. |
| 6,597,937 | B2 | 7/2003 | Liu et al. |
| 2003/0013953 | A1 | 1/2003 | Mistretta |
| 2004/0082846 | A1 | 4/2004 | Johnson et al. |

(Continued)

FOREIGN PATENT DOCUMENTS

| | | |
|---|---|---|
| EP | 2087843 A1 | 8/2009 |
| WO | 2007046025 A2 | 4/2007 |

(Continued)

*Primary Examiner* — Joseph M Santos Rodriguez (57) ABSTRACT

A method includes scanning a region of interest, during a contrast agent based perfusion scan, at a predetermined temporal sampling rate during contrast agent uptake in the region of interest, and generating time frame data indicative of the scanned region of interest. The method further includes identifying a predetermined change in an amount of the contrast agent in the region of interest from the time frame data. The method further includes scanning the region of interest at a lower temporal sampling rate, which is lower than the temporal sampling rate during the contrast agent uptake, in response to identifying the predetermined change in the amount of the contrast agent in the region of interest.

24 Claims, 7 Drawing Sheets

(56) References Cited

U.S. PATENT DOCUMENTS

2009/0202035 A1* 8/2009 Tsukagoshi ............ A61B 6/032
378/8
2010/0292570 A1* 11/2010 Tsukagoshi ............ A61B 6/032
600/431

FOREIGN PATENT DOCUMENTS

WO  2008120119 A1  10/2008
WO  2009115935 A1  9/2009

* cited by examiner

ABSTRACT
DYNAMIC PERFUSION IMAGING

CROSS-REFERENCE TO PRIOR APPLICATIONS

This application is the U.S. National Phase application under 35 U.S.C. §371 of International Application No. PCT/IB2012/051914, filed on Apr. 17, 2012, which claims the benefit of U.S. Provisional Application No. 61/476,642 filed on Apr. 18, 2011 These applications are hereby incorporated by reference herein in their entirety.

FIELD OF THE INVENTION

The following generally relates to dynamic perfusion imaging and is described with application to computed tomography (CT); however, the following is also amenable to other imaging modalities.

BACKGROUND OF THE INVENTION

Perfusion imaging is an imaging technique which captures the transit of an administered contrast agent through vascular tissue of interest such as a vessel and/or an organ like the heart. Generally, for perfusion imaging, a contrast agent bolus is administered to a patient, and the region of interest of the patient including the vascular tissue of interest is scanned. The contrast agent causes the x-ray density in the vascular tissue of interest to temporarily increase as the contrast agent flows through the vascular tissue. A typical perfusion scan includes acquiring data of the same region, over multiple time intervals, covering contrast agent arrival, uptake and wash out. For cardiac applications, the scan has included acquiring data of the same cardiac phase.

Analysis of the acquired data can be used to determine a perfusion state of the vascular tissue of interest, for example, based on the observations of the contrast agent dynamics in the scan field of view. For cardiac applications, this may include quantifying the contrast agent distribution in the cardiac muscle over time. Such analysis may include determining various perfusion related information for the vascular tissue of interest such as a time-attenuation curve, blood flow, blood volume, mean transit time, maximum upslope, time to peak, etc. This information can be used to identify ischemic tissue and/or differentiate between irreversibly damaged (or necrotic) tissue and potentially reversibly damaged (or at-risk) tissue.

Traditional perfusion imaging included continuously scanning the region of interest from before contrast arrival through contrast washout. More recent perfusion imaging has included temporal intermittent, at equal temporal distances, scanning of the region of interest from contrast arrival through contrast washout. Generally, the frequency of the temporal intermittent sampling is based on the temporal sampling necessary to obtain data suitable for accurately deriving perfusion parameters such as time to peak, maximum upslope, and/or other relevant perfusion parameters. For cardiac applications, this has included scanning during one or more particular cardiac motion phases of interest (e.g., such as a quiet phase) each or every other cardiac cycle.

Unfortunately, computed tomography perfusion imaging exposes the patient to ionizing radiation, which can kill or damage cells and which may increase risk of cancer, and the deposited dose with both continuous and temporal intermittent imaging is considered high, and such imaging generally is not used for screening and/or in routine clinical practice. Furthermore, patients who undergo such imaging typically undergo several follow-up imaging procedures, which increases the cumulative radiation dose. Moreover, simply reducing the temporal intermittent sampling may introduce error in perfusion parameters. Thus, there is an unresolved need for other approaches to further reduce patient dose with perfusion imaging.

SUMMARY OF THE INVENTION

Aspects of the present application address the above-referenced matters and others.

According to one aspect, a method includes scanning a region of interest, during a contrast agent based perfusion scan, at a predetermined temporal sampling rate during contrast agent uptake in the region of interest, and generating time frame data indicative of the scanned region of interest. The method further includes identifying a predetermined change in an amount of the contrast agent in the region of interest from the time frame data. The method further includes scanning the region of interest at a lower temporal sampling rate, which is lower than the temporal sampling rate during the contrast agent uptake, in response to identifying the predetermined change in the amount of the contrast agent in the region of interest.

In another aspect, a system includes a contrast agent detector with a contrast identifier that identifies a presence of contrast agent in time frame perfusion scan acquisition data and generates a contrast signal indicating the presence of the contrast agent in the time frame acquisition data. The contrast signal is used to vary a temporal sampling rate between a lower temporal sampling rate when the contrast agent is not present in the time frame data and a higher temporal sampling rate when the contrast agent is present in the time frame data.

In another aspect, a computer readable instructions encoded on computer readable medium, which, when executed by a processor of a computing system causes the processor to: vary a temporal sampling rate of data acquisition during a perfusion scan based on a state of contrast agent in resulting acquisition time frame data, wherein the temporal sampling rate is at least varied between contrast agent uptake and contrast agent washout based on a contrast agent level determined using a model based segmentation of the time frame data.

Still further aspects of the present invention will be appreciated to those of ordinary skill in the art upon reading and understand the following detailed description.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

Figure 1:
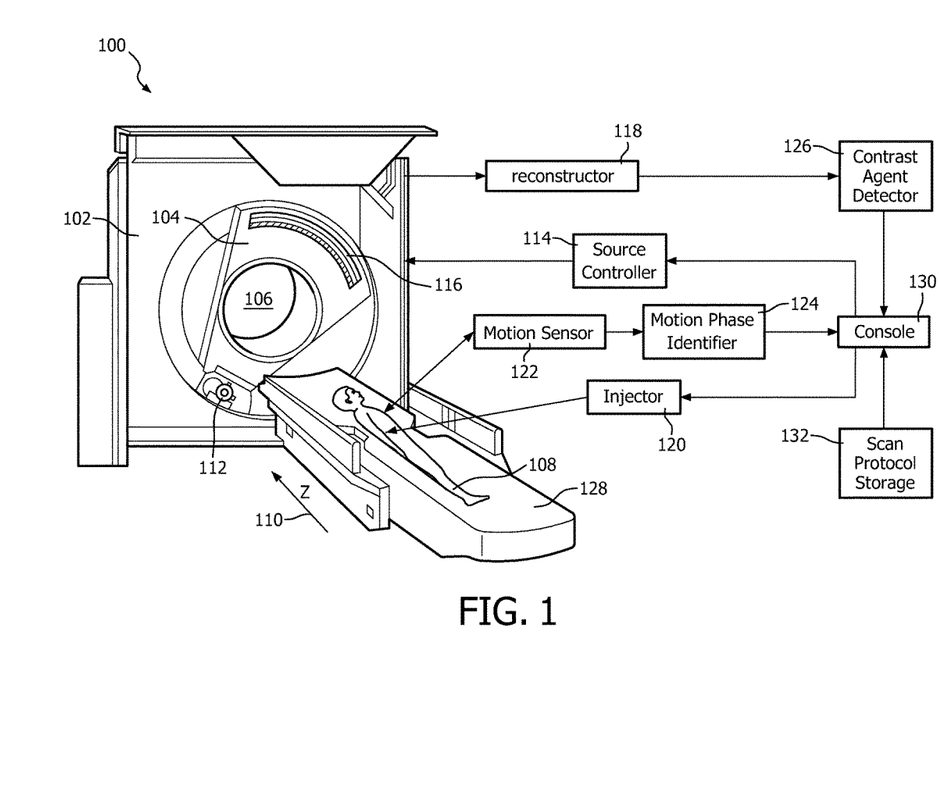
FIG. 1 schematically illustrates an example imaging system in which temporal sampling for perfusion imaging is selectively and dynamically varied over time based on a contrast level in the time frame acquisition data.

FIG. 1 illustrates an imaging system 100 such as a computed tomography (CT) scanner.

The imaging system 100 includes a stationary gantry 102 and a rotating gantry 104, which is rotatably supported by the stationary gantry 102. The rotating gantry 104 rotates around an examination region 106, and a portion of an object or subject 108 therein, about a longitudinal or z-axis 110.

A radiation source 112, such as an x-ray tube, is supported by and rotates with the rotating gantry 104 around the examination region 106. The radiation source 112 emits radiation that is collimated to form a generally fan, wedge, or cone shaped radiation beam that traverses the examination region 106.

A source controller 114 controls the radiation source 112. This includes activating the source 112 to emit radiation during time series perfusion imaging to acquire time frame data. Such activation can be temporally continuous or temporally intermittent during an imaging examination for one or more rotations of the source 112, including for the entire or a sub-portion of each rotation of the source 112.

A radiation sensitive detector array 116 detects photons emitted by the radiation source 112 that traverse the examination region 106 and generates projection data indicative of the detected radiation. The radiation sensitive detector array 116 may include one or a two dimensional detector array.

A reconstructor 118 reconstructs the projection data and generates time series volumetric image data indicative of the examination region 106. Various reconstruction algorithms can be employed such as filtered backprojection, statistical, iterative, sparse sampling, and/or other reconstruction algorithms.

An injector 120 is configured to inject or administer a material such as one or more contrast agents to the subject 108 or an object (e.g., a phantom) to be scanned. A contrast agent can additionally or alternatively be manually administered by a clinician or the like. Where the contrast agent is manually administered to the subject 108, the injector 120 can be omitted.

A motion sensor 122 detects motion of moving structure of the subject 108 and generates a motion signal indicative thereof. Examples of moving structure include the heart, the lungs, and/or other moving structure. For cardiac applications, the motion sensor 122 may include an electrocardiograph (ECG), and for respiratory applications, the motion sensor 122 may include a respiratory belt, light emitting landmarks, etc. Where motion is not taken into account during scanning, the motion sensor 122 can be omitted.

A motion phase identifier 124 identifies a motion state(s) in the motion signal and generates a motion phase signal indicative thereof. For cardiac applications, this may include identifying a time duration of a cardiac cycle, identifying a landmark in the cardiac cycle such as an "R" wave, and then identifying a phase based on a predetermined percentage (e.g., 40%, 70%, etc.) of the cardiac cycle and the "R" wave. The phase may be a quiet state where cardiac motion is lower relative to other states or another phase.

A contrast agent detector 126 generates a signal indicative of a presence of a contrast agent and/or a contrast agent level in the acquisition time frame data. As described in greater detail below, in one non-limiting instance, this includes determining the pixel intensity of structure, a sub-set of the structure, or a sub-region of a sub-set of the structure in the acquisition time frame data, based on a model for the structure and/or otherwise.

A subject support 128, such as a couch, supports the subject 108 or an object in the examination region 106 and is movable along the x, y and z-axis directions in coordination with the rotation of the rotating gantry 104 to facilitate helical, axial, or other desired scanning trajectories.

A general purpose computing system serves as an operator console 130. Software resident on the console 130 and executed by a processor allows an operator to control operation of the system 100, for example, by allowing the operator to employ a scan protocol from scan protocol storage 132 such as a (motion phase or non-motion phase based) adaptive temporal sampling dynamic perfusion scan protocol.

As described in greater detail below, one such protocol includes dynamically adjusting the temporal sampling during a perfusion scan based on the contrast in the acquisition time frame data. This allows acquiring data at a lower temporal sampling during pre-contrast uptake and/or contrast washout, and a higher temporal sampling (suitable for determining relevant perfusion parameters) during contrast uptake. This may facilitate decreasing dose relative to a configuration in which a single temporal sampling is used throughout pre-contrast uptake, contrast uptake and contrast washout.

For a motion phase based perfusion scan such as a cardiac perfusion scan, data acquisition may also include acquiring data for an entire or for one or more phases (e.g., systole and/or diastole, and/or a portion thereof) of a cardiac cycle for a time frame acquisition. The motion phase signal from the motion phase identifier 124 can be used to trigger data acquisition within a cardiac cycle based on cardiac phase. Scanning only during a sub-portion (or phase) of a cardiac cycle may further reduce dose relative to scanning during the entire cardiac cycle.

Dose can be further reduced through reducing spatial sampling and/or tube current. For spatial sampling, this includes reducing the spatial sampling to a sparse sampling and using any known or other sparse sampling reconstruction algorithms to reconstruct the data. In one instance, the sparse spatial sampling can be about one tenth of full spatial sampling. Tube current can be reduced during pre-contrast uptake and/or contrast washout. In one instance, the tube current can be reduced to about one third of that used during contrast uptake.

Figure 2:
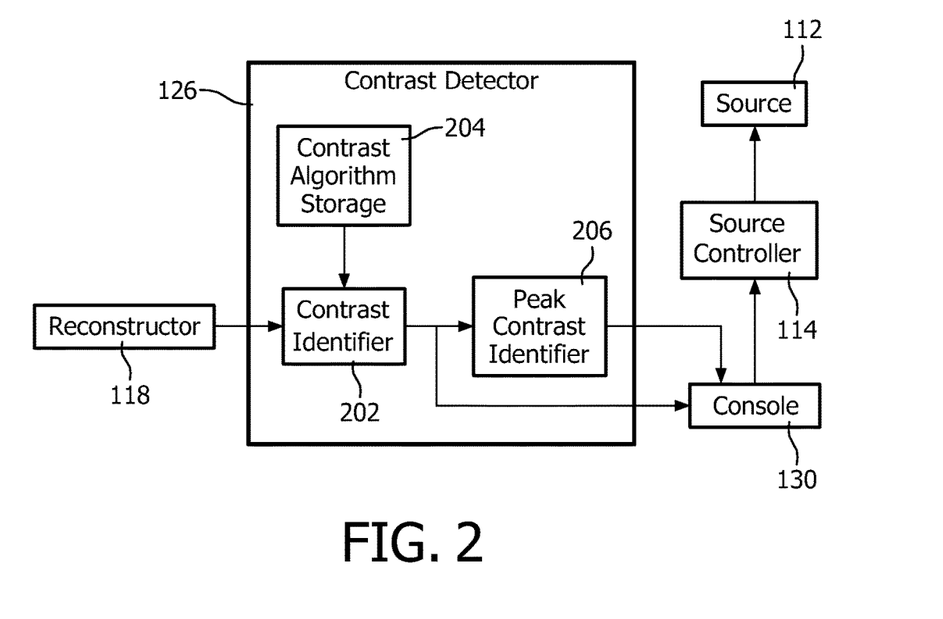
FIG. 2 schematically illustrates an example contrast detector for detecting contrast presence and/or level in the time frame acquisition data.

FIG. 2 schematically illustrates an example of the contrast agent detector 126 in connection with the source 112, the source controller 114, the reconstructor 118, and the console 130.

The illustrated contrast agent detector 126 includes a contrast identifier 202, which is configured to evaluate the acquisition time frame data and generate a contrast signal indicative of a presence (and/or absence) and/or a degree of contrast in the data, for example, based on a contrast identification algorithm from a contrast algorithm storage 204.

By way of non-limiting example, with one contrast identification algorithm, the contrast identifier 202 determines an average pixel intensity of structure in acquisition time frame data. The contrast identifier 202 then compares the determined intensity with a baseline threshold intensity. In this instance, if the determined intensity satisfies the threshold, the contrast identifier 202 generates a contrast signal indicating that contrast is present. Otherwise, the contrast identifier 202 may not generate a contrast signal or may generate a contrast signal that indicates contrast is not present (or is absent).

With another contrast identification algorithm, the contrast identifier 202 employs an anatomical model based segmentation approach to segment the acquisition time frame data into sub-structure (e.g., heart, lungs, etc.). The contrast identifier 202 then determines an average pixel intensity of a sub-set of the sub-structure, and compares the intensity with the threshold. Likewise, the contrast identifier 202 generates the contrast signal indicating that contrast is present and either generates the contrast signal indicating that contrast is absence or does not generate the signal.

Figure 3:
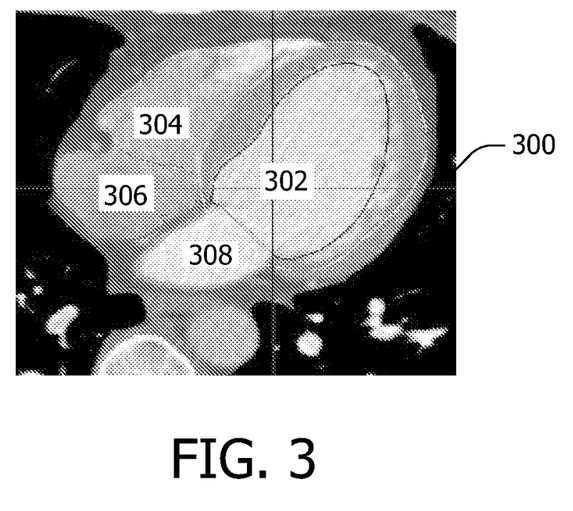
FIG. 3 graphically illustrates an example model approach for detecting the contrast presence and/or contrast level.

In yet another algorithm, the contrast identifier 202 further segments sub-structure (e.g., the heart) into sub-regions (e.g., left ventricle, right ventricle, left atrium, right atrium, etc.) based in the model. An example of this is shown in FIG. 3, which graphically illustrates an image 300 of a heart segmented into sub-regions 302, 304, 306 and 308. The contrast identifier 202 determines an average pixel intensity of one or more of the sub-regions (e.g., the sub-region reached last by the contrast), compares the intensity with the predetermined threshold, and generates the contrast signal as discussed above based thereon.

Other approaches for identifying the presence and/or level of contrast are also contemplated herein.

A peak contrast identifier 206 is configured to evaluate the contrast signal and generate a peak contrast signal in response to identifying a peak contrast from the contrast signal. Various approaches can be used to identify the peak. By way of non-limiting example, the peak contrast identifier 206 can identify the peak based on a comparison of consecutively determined contrast levels, a contrast level rate of change, and/or other approaches.

The contrast agent detector 126 conveys the contrast signal and/or the peak contrast signal, individual or in combination as the signal output by the contrast agent detector 126, to the console 130, which employs the signal to control the source controller 114 to activate the source 112 so as to adapt the temporal sampling during perfusion imaging.

Figure 4:
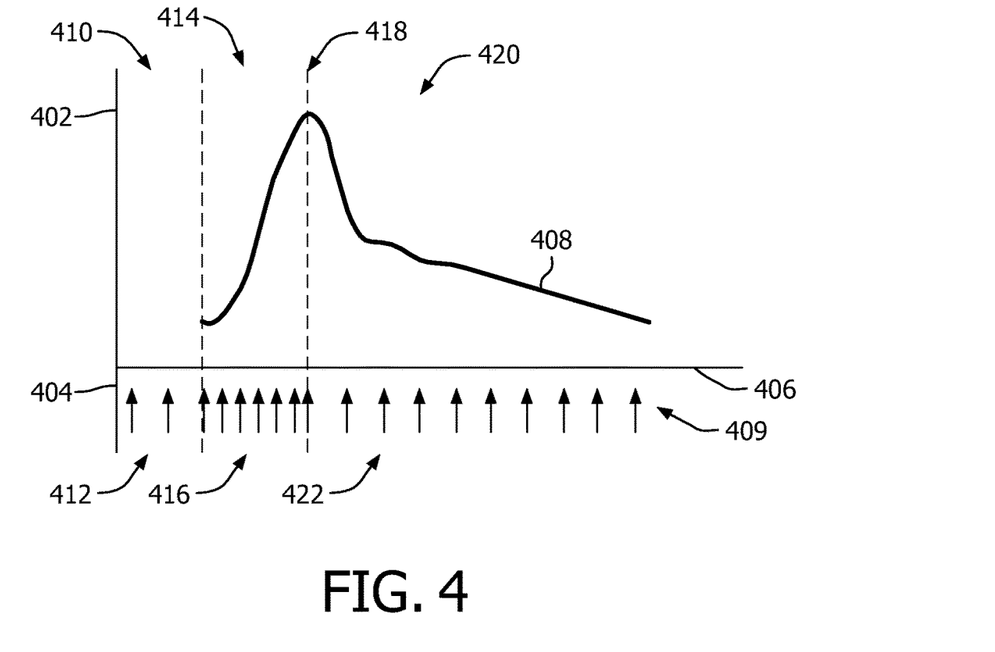
FIG. 4 graphically illustrates example temporal sampling for a cardiac perfusion scan in which different but constant temporal sampling respectively is used during pre-contrast uptake, contrast uptake and contrast washout based on a contrast level profile.

FIG. 4 graphically illustrates an example of varying temporal sampling during a perfusion scan in connection with FIGS. 2 and 3.

A y-axis includes an upper portion 402 that represents the amount (density) of contrast and a lower portion 404 that represents image acquisition, an x-axis 406 represents time, a profile 408 represents contrast uptake and wash out as a function of time, and a profile 409 represents temporal sampling (or, data acquisition as a function of time).

A region 410 represents a region in which contrast has been administered but has not yet reached the region of interest being scanned and no contrast has been detected. In this example, during this region, the source controller 114 controls the source 112 to emit radiation at a first or pre-contrast uptake temporal sampling 412.

The temporal sampling 412 can be lower in this region, relative to the temporal sampling during uptake, since this region is primarily used to establish a baseline intensity in order to identify when contrast reaches the scanned region of interest. The lower sampling reduces dose in this region relative to using the same temporal sampling as that used during contrast uptake. Tube current can also be reduced for this region.

A region 414 represents a region in which contrast reaches the scanned region of interest and the signal from the contrast agent detector 126 (e.g., the contrast signal from the contrast identifier 202) indicates a presence of contrast in the scanned region of interest. In this example, during this region, the source controller 114 controls the source 112 to emit radiation at a second or contrast uptake temporal sampling 416.

The temporal sampling 416 that is used for perfusion scanning to acquire data at a temporal sampling at which the relevant perfusion information (e.g., time to peak, maximum upslope, etc.) can be determined for the region 414. In the case of cardiac perfusion, the temporal sampling 416 can be based on an average heart cycle of the patient being scanned. By way of example, the temporal sampling 416 may be on the order of every heart cycle to every other heart cycle (e.g., 1 to 2 seconds).

A region 418 represents a region in which peak contrast is identified by the contrast agent detector 126 (e.g., the peak contrast signal from the peak contrast identifier 206).

A region 420 represents a region in which contrast washes out of the scanned region of interest and the signal from the contrast agent detector 126 (e.g., the contrast signal from the contrast identifier 202) indicates a decreasing presence of contrast in the scanned region of interest. In this example, during this region, the source controller 114 controls the source 112 to emit radiation at a third or contrast washout temporal sampling 422, which is equal to or greater than the first temporal sampling 412 and lower than the second temporal sampling 416.

Generally, with this approach, temporal sampling for image acquisition is adapted to a perfusion time curve (FIG. 4), where the temporal sampling is more dense during contrast uptake (the upslope in FIG. 4) and less dense than during contrast uptake for pre-contrast uptake and contrast wash out (the downslope in FIG. 4), and the decision on when to use which sampling pattern is based on a model based image analysis (FIGS. 2 and 3) using pixel intensity of certain structures.

Variations are contemplated.

Figure 5:
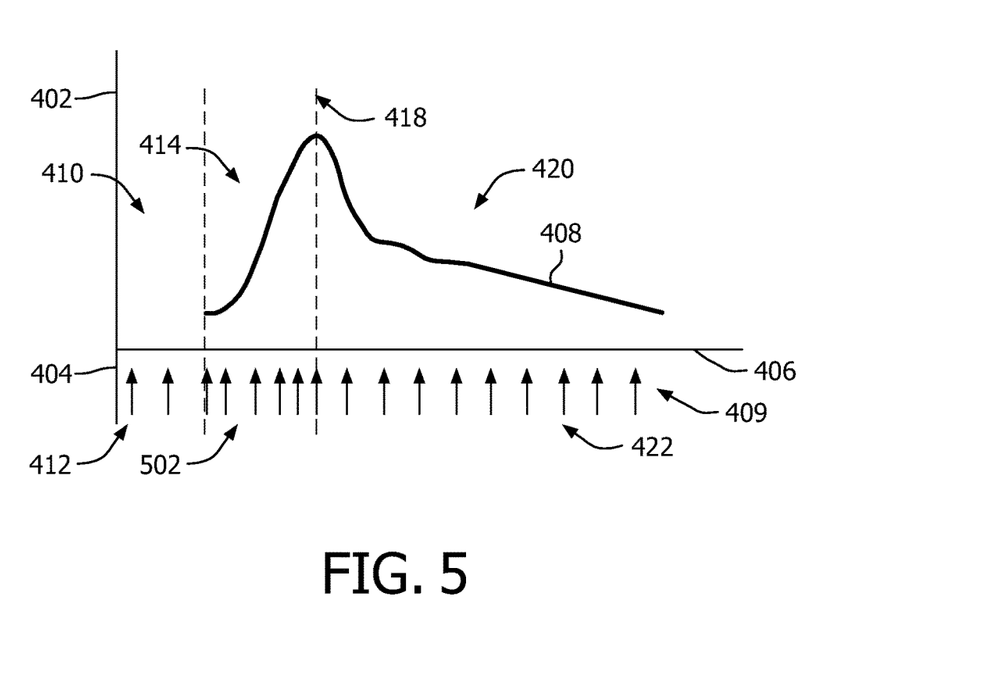
FIG. 5 graphically illustrates example temporal sampling for a cardiac perfusion scan in which the temporal sampling during contrast uptake is varied over time.

FIG. 5 graphically illustrates another example of varying temporal sampling during a perfusion scan. FIG. 5 is substantially similar to FIG. 4; however, in FIG. 5, a varying temporal sampling 502 is used during contrast uptake.

Figure 6:
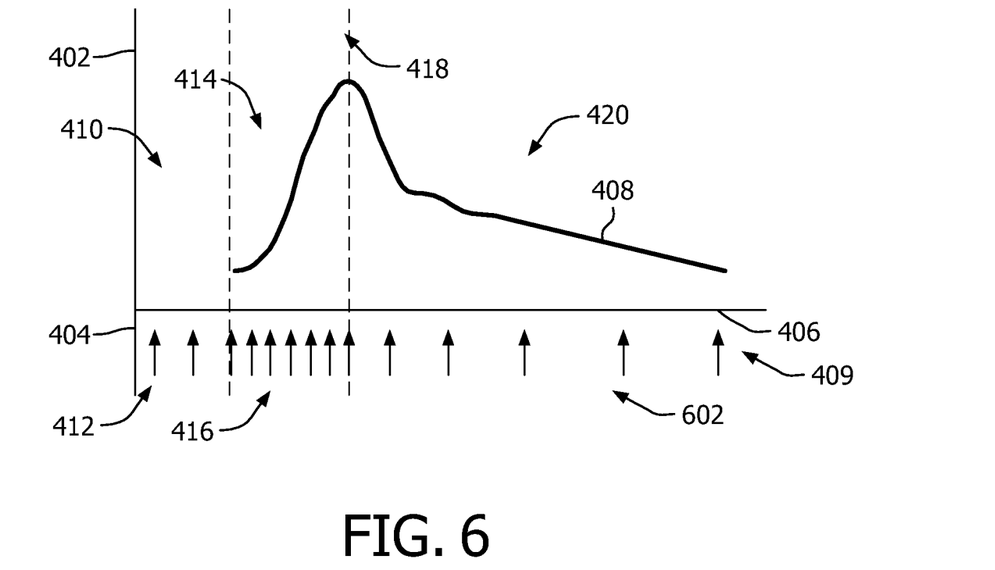
FIG. 6 graphically illustrates example temporal sampling for a cardiac perfusion scan in which the temporal sampling during contrast washout is varied over time.

FIG. 6 graphically illustrates another example of varying temporal sampling during a perfusion scan. FIG. 6 is also substantially similar to FIG. 4; however, in FIG. 6, a varying temporal sampling 602 is used during contrast washout.

Figure 7:
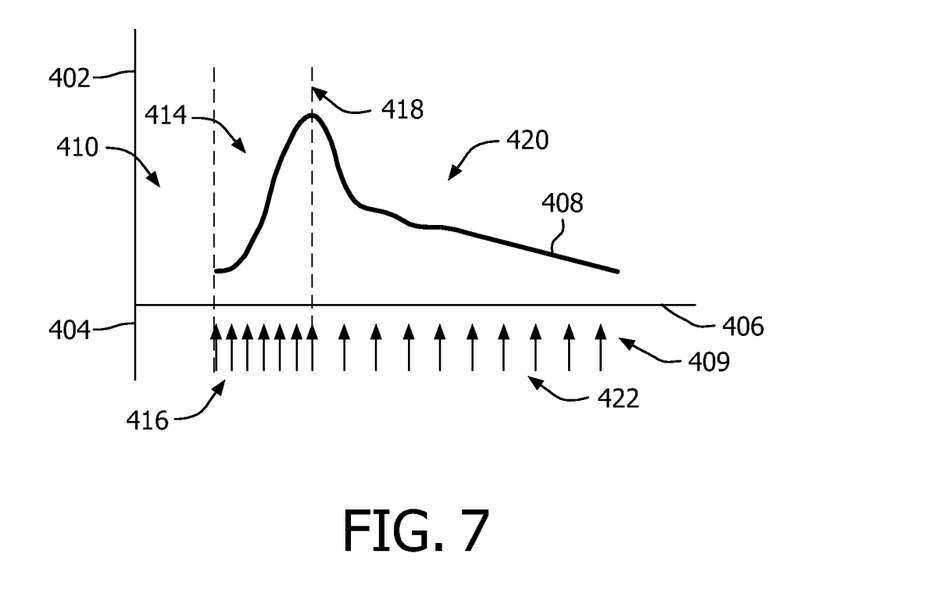
FIG. 7 graphically illustrates example of temporal sampling for a cardiac perfusion scan in which temporal sampling begins at contrast uptake.

FIG. 7 is substantially similar to FIG. 4 except that scanning is not performed during the pre-contrast uptake region 410. Instead, data acquisition begins after lapse of a predetermined time delay from administration of the contrast agent, which can be determined based on a test bolus, a previous perfusion scan of the patient, historical perfusion scans for other patients, and/or otherwise.

In another variation, the temporal sampling is a combination of FIGS. 4, 5, 6, and/or 7 and/or other temporal sampling.

In the illustrated embodiment, the contrast agent identifier 126 evaluates the reconstructed time frame data. In a variation, the contrast agent identifier 126 can evaluate the projection data, individually and/or in connection with the reconstructed time frame data, and generates the contrast signal.

In the illustrated embodiment, the motion phase identifier 124 evaluates the motion signal to identify one or more motion states therein. In a variation, the motion phase identifier 124 evaluates the projection data, individually and/or in connection with the reconstructed time frame data, to identify the one or more motion states. This may include comparing successively acquired time frames (e.g., determining a difference image) to identify quiet, similar, and/or other motion phases.

Figure 8:
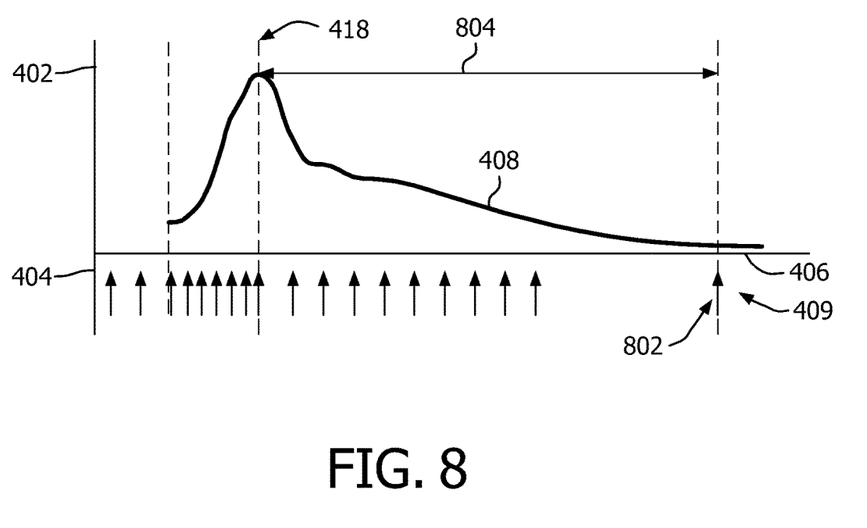
FIG. 8 graphically illustrates example of temporal sampling for a late enhancement scan.

In another variation, the contrast uptake temporal sampling can be extended beyond peak contrast, for example, by a predetermined temporal delay, for example, in order to scan late enhancement at the contrast uptake temporal sampling. FIG. 8 shows an example of a late enhancement scan 802 at a fixed temporal distance 804 from the peak 418. In other embodiments, the fixed temporal distance 804 can be from another parameter such as maximum upslope, time to maximum upslope, or any other parameter. The scan data for the late enhancement can be used to identify irreversibly damaged tissue.

In FIGS. 2 and 3, the peak contrast identifier 206 was used to identify a peak contrast level, and then the temporal sampling was changed. In another instance, the data is analyzed to locate when a predetermined level of contrast has been reached in the image 300 and/or sub-regions 302-308. In this instance, the temporal sampling is changed in response to the predetermined level of contrast reaching the predetermined level of contrast. In yet another instance, the data is analyzed to determine when a contrast level of a predetermined one or more of the sub-regions 302-308 reaches or exceeds (or falls below) a contrast level of one or more of the other sub-regions 302-308. In this instance, the temporal sampling is changed in response to the relationship of level of contrast between the sub-regions satisfying the condition.

Figure 9:
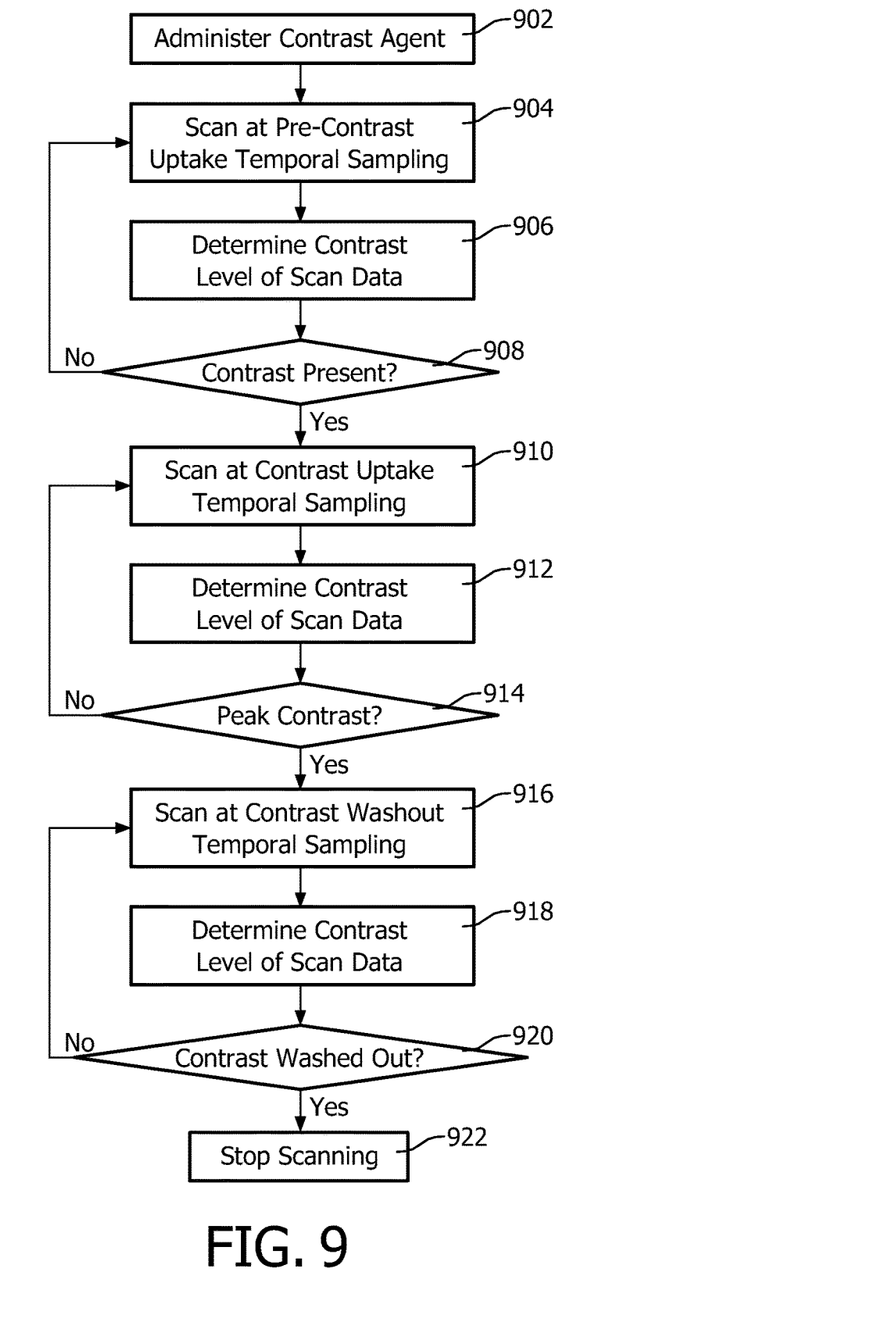
FIG. 9 illustrates a flow chart for varying temporal sampling of perfusion imaging over time based on a contrast level in the time frame acquisition data.

FIG. 9 illustrates an example perfusion imaging flow chart.

It is to be appreciated that the ordering of the acts is not limiting. As such, in other embodiment, the order may be different, including concurrent. Furthermore, one or more of the acts may be omitted and/or one or more acts can be added.

At 902, a contrast agent is administered to a subject.

At 904, a region of interest of the subject is scanned based on a pre-contrast uptake temporal sampling. By way of non-limiting example, with cardiac perfusion imaging, the subject may be scanned to acquire data at least during a sub-portion of every fifth cardiac cycle. The sub-portion may correspond to one or more particular motion phases of structure of interest of the region of interest. The tube current may also be set to a pre-contrast uptake level.

At 906, the contrast level of the acquisition time frame scan data is determined. As described herein, the level of contrast can be determined based on an average pixel intensity of the structure in the data, an average pixel intensity of a sub-set of the structure in the data, an average pixel intensity of one or more sub-regions of the sub-set of the structure, and/or otherwise. The intensity of initial data is used to determine a baseline non-contrast level.

At 908, it is determined whether contrast is present in the acquisition time frame scan data based on the contrast level and the baseline non-contrast level. In one instance, this is achieved by comparing the contrast level with the baseline non-contrast level.

If the administered contrast is not present in the acquisition time frame data (e.g., the contrast level is less than or within a predetermined tolerance of the baseline non-contrast level), then acts 904-908 are repeated.

If the administered contrast is present in the acquisition time frame data (e.g., the contrast level is greater than the baseline non-contrast level with the predetermined tolerance), then at 910, the region of interest of the subject is scanned based on a predetermined contrast uptake temporal sampling, which is greater than the pre-contrast uptake temporal sampling. By way of non-limiting example, with cardiac perfusion imaging, the contrast uptake temporal sampling may be every or every other cardiac cycle.

At 912, the contrast level of the acquisition time frame data is determined, for example, as discussed in connection with act 906.

At 914, it is determined whether peak contrast uptake is reached based on the acquisition time frame data. This can be achieved by comparing the current contrast level with the previously determined contrast level and detecting a decreasing contrast level, and/or otherwise.

If the peak contrast level is not reached in the acquisition time frame data, then acts 910-914 are repeated.

If the peak contrast is reached in the acquisition time frame data, then at 916, the region of interest of the subject is scanned based on a predetermined contrast washout temporal sampling, which is less than the contrast uptake temporal sampling. By way of non-limiting example, with cardiac perfusion imaging, the contrast washout temporal sampling may be every fifth cardiac cycle.

At 918, the contrast level of the acquisition time frame data is determined, for example, as discussed in connection with acts 906 and 912.

At 920, it is determined whether the contrast washed out of the region of interest. This can be achieved by comparing the contrast level with the baseline non-contrast level.

If the contrast is still present in the acquisition time frame data, then acts 916-920 are repeated.

If contrast is not present in the acquisition time frame data, then at 922, scanning is stopped.

The above may be implemented by way of computer readable instructions, which when executed by a computer processor(s), cause the processor(s) to carry out the described acts. In such a case, the instructions are stored in a computer readable storage medium associated with or otherwise accessible to the relevant computer. The acts need not be performed concurrently with data acquisition.

Although the above has been described in connection with a conventional scanner, it is to be understood that the system 100 may include a spectral CT scanner. Such a scanner may include one or more of the following: multiple x-ray tubes configured to emit radiation having different emission spectra, tube voltage switching circuitry configured to switch an x-ray tube of the system between at least two different emission spectra, and/or an energy resolving detector (e.g., a photon counting detector, a detector with a plurality of scintillator/photodiode pairs, each configured to detect photons within a different predetermined energy range). In this instance, the perfusion data represent contrast agent concentration per tissue volume, and the concentration can be determined by multi-energy imaging, material separation, and/or k-edge imaging.

The invention has been described herein with reference to the various embodiments. Modifications and alterations may occur to others upon reading the description herein. It is intended that the invention be construed as including all such modifications and alterations insofar as they come within the scope of the appended claims or the equivalents thereof.

What is claimed is:

1. A method, comprising:
   scanning a region of interest with an imaging system, during a contrast agent based perfusion scan, at a temporal sampling rate during contrast agent uptake in the region of interest, and generating time frame data indicative of the scanned region of interest with a reconstructor;
   determining a change in an amount of contrast agent in the region of interest from the time frame data with a contrast detector;
   generating a contrast signal indicating the change in the amount of contrast agent in the region of interest from the time frame data with the contrast detector; and
   scanning the region of interest with the imaging system at a lower temporal sampling rate, which is lower than the temporal sampling rate during the contrast agent uptake, in response to the generated contrast signal indicating the change in the amount of the contrast agent in the region of interest,
   wherein the lower temporal sampling rate varies during scanning the region of interest.

2. The method of claim 1, wherein the change is a decrease in the amount of the contrast agent, wherein the decrease is indicative of contrast agent washout.

3. The method of claim 1, further comprising:
   determining an average pixel intensity of structure in the time frame data;
   comparing the average pixel intensity with an average pixel intensity of previous time frame data; and
   determining the change in the amount of contrast agent in the region of interest based on a result of the comparison.

4. The method of claim 1, further comprising:
   segmenting the time frame data into sub-structure;
   determining an average pixel intensity of a sub-set of the sub-structure;
   comparing the average pixel intensity with an average pixel intensity of corresponding previous time frame data; and
   determining the change in the amount of contrast agent in the region of interest based on a result of the comparison.

5. The method of claim 1, further comprising:
   segmenting the time frame data into sub-structure;
   segmenting at least one sub-structure into sub-regions;
   determining an average pixel intensity of a sub-set of the sub-regions;
   comparing the average pixel intensity with an average pixel intensity of corresponding previous time frame data; and
   determining the change in the amount of contrast agent in the region of interest based on a result of the comparison.

6. The method of claim 3, further comprising:
   determining the change in the amount of the contrast agent in the region of interest in response to the average pixel intensity of previous time frame data exceeding the average pixel intensity of the time frame data.

7. The method of claim 1, further comprising:
   segmenting the time frame data into sub-structure;
   segmenting at least one sub-structure into sub-regions;
   determining an average pixel intensity of at least one of the sub-regions;
   determining an average pixel intensity of at least another of the sub-regions;
   comparing the average pixel intensities; and
   determining the change in the amount of contrast agent in the region of interest based on a result of the comparison.

8. The method of claim 1, further comprising:
   performing a data acquisition at a predetermined fixed temporal distance from the change in the amount of contrast agent in the region of interest to capture late contrast agent enhancement.

9. The method of claim 1, further comprising:
   scanning the region of interest at a second lower temporal sampling rate before the contrast agent uptake in the region of interest, and generating time frame data indicative of the scanned region of interest;
   determining a presence of the contrast agent in the region of interest from the time frame data; and
   scanning the region of interest at the predetermined temporal sampling rate, in response to determining the presence of the contrast agent in the region of interest.

10. The method of claim 1, further comprising:
    sensing a motion cycle of the region of interest;
    identifying a sub-portion of the motion cycle; and
    scanning the region of interest only during the sub-portion of the motion cycle.

11. The method of claim 10, wherein the sub-portion corresponds to a lower motion phase of the motion cycle, and further comprising:
    scanning the region of interest during at least two of the sub-portions.

12. The method of claim 1, wherein the predetermined temporal sampling rate varies during contrast agent uptake in the region of interest.

13. The method of claim 1, further comprising:
    scanning using a sparse spatial sampling; and
    reconstructing the time frame data using a sparse reconstruction algorithm.

14. The method of claim 1, further comprising:
    using a lower tube current during at least one of pre-contrast agent uptake scanning or contrast agent washout scanning and using a higher tube current during contrast agent uptake scanning, wherein the higher tube current is greater than the lower tube current.

15. A system, comprising:
    an imaging system that performs a perfusion scan that generates time frame perfusion scan acquisition data; and
    a contrast agent detector, including:
       a contrast identifier that determines a presence of a contrast agent in the time frame perfusion scan acquisition data and generates a contrast signal indicating the presence of the contrast agent in the time frame acquisition data,
       wherein the contrast signal is used by an imaging system controller to vary a temporal sampling rate between a lower temporal sampling rate when the contrast agent is not present in the time frame data and a higher temporal sampling rate when the contrast agent is present in the time frame data.

16. The system of claim 15, wherein the contrast agent identifier determines the presence of contrast agent in the time frame acquisition data using a model based segmentation approach.

17. The system of claim 16, wherein the model based segmentation approach segments a structure of interest into sub-regions, and the contrast identifier determines the presence of the contrast agent in a sub-set of the sub-regions.

18. The system of claim 16, wherein the contrast agent identifier determines the presence of the contrast agent based on pixel intensity.

19. The system of claim 15, the contrast agent detector further comprising:

a peak contrast identifier that determines a peak degree of contrast agent in the time frame acquisition data and generates a peak contrast signal indicating the peak degree of contrast agent in the time frame acquisition data, wherein the peak contrast signal is used to vary the higher temporal sampling rate from a first higher temporal sampling rate before the peak degree of contrast agent in the time frame acquisition data and a second higher temporal sampling rate after the peak degree of contrast agent in the time frame acquisition data in response to the peak contrast signal, wherein the first higher temporal sampling rate is greater than the second higher temporal sampling rate.

20. The system of claim 15, wherein the imaging system is a spectral computed tomography scanner.

21. The system of claim 20, wherein a concentration of contrast agent level is determined through material separation and/or k-edge imaging.

22. The system of claim 19, wherein the first higher temporal sampling rate varies.

23. The system of claim 19, wherein the second higher temporal sampling rate varies.

24. A method, comprising:

scanning a region of interest with an imaging system, during a contrast agent based perfusion scan, at a temporal sampling rate in the region of interest, and generating time frame data indicative of the scanned region of interest with a reconstructor;

determining a presence of the contrast agent in the region of interest from the time frame data with a contrast detector;

generating a contrast signal indicating the presence of the contrast agent in the region of interest from the time frame data with the contrast detector; and scanning the region of interest with the imaging system, wherein the contrast signal is used by an imaging system controller to vary the temporal sampling rate between a lower temporal sampling rate when the contrast agent is not present in the time frame data and a higher temporal sampling rate when the contrast agent is present in the time frame data.

* * * * *